(12) United States Patent
Wright

(10) Patent No.: US 7,055,910 B2
(45) Date of Patent: Jun. 6, 2006

(54) PHLEBOTOMY ARMREST ASSEMBLY AND METHOD OF USING SAME

(75) Inventor: Clifford A. Wright, San Diego, CA (US)

(73) Assignee: Medical Device Group, Inc., Poway, CA (US)

( * ) Notice: Subject to any disclaimer, the term of this patent is extended or adjusted under 35 U.S.C. 154(b) by 0 days.

(21) Appl. No.: 10/655,148

(22) Filed: Sep. 4, 2003

(65) Prior Publication Data

US 2005/0052066 A1  Mar. 10, 2005

(51) Int. Cl.
*A47C 7/54* (2006.01)

(52) U.S. Cl. ............................ 297/411.35; 297/411.23; 297/411.36; 297/411.37; 297/411.38; 403/90

(58) Field of Classification Search ........... 297/411.23, 297/411.35, 411.36, 411.37, 411.38; 403/56, 403/76, 90, 114, 143
See application file for complete search history.

(56) References Cited

U.S. PATENT DOCUMENTS

| | | | | |
|---|---|---|---|---|
| 169,383 | A | * | 11/1875 | Starr ............................ 403/90 |
| 470,668 | A | * | 3/1892 | Fisher ............................ 108/8 |
| 490,541 | A | * | 1/1893 | Case ............................ 297/405 |
| 1,706,634 | A | * | 3/1929 | Seils ..................... 294/411.22 |
| 3,556,092 | A | | 1/1971 | Eisenberg |
| 3,614,085 | A | * | 10/1971 | Cunningham .................. 5/623 |
| 3,640,273 | A | | 2/1972 | Ray |
| 3,724,456 | A | | 4/1973 | Waxman |
| 3,812,851 | A | | 5/1974 | Rodriguez |
| 3,896,799 | A | | 7/1975 | Seeley |
| 3,901,227 | A | | 8/1975 | Klatskin |
| 3,910,538 | A | * | 10/1975 | Baitella .................... 248/124.1 |
| 4,043,330 | A | | 8/1977 | Bansal |
| 4,277,102 | A | * | 7/1981 | Aaras et al. ........... 297/411.36 |
| 4,286,588 | A | | 9/1981 | Lovegrove |
| D263,423 | S | | 3/1982 | Aslanian |
| 4,369,774 | A | | 1/1983 | Robbins |
| 4,488,715 | A | | 12/1984 | Comeau |
| 4,503,849 | A | | 3/1985 | Morgan et al. |
| 4,698,837 | A | | 10/1987 | Van Steenburg |
| 4,708,510 | A | * | 11/1987 | McConnell et al. .......... 403/90 |
| 4,840,168 | A | | 6/1989 | Lonardo |
| 4,913,393 | A | * | 4/1990 | Wood ....................... 248/230.2 |
| 4,928,712 | A | | 5/1990 | Mele |
| 4,941,480 | A | | 7/1990 | McLean et al. |
| 4,945,925 | A | | 8/1990 | Garcia |
| 5,025,801 | A | | 6/1991 | Callaway |
| 5,029,941 | A | * | 7/1991 | Twisselmann ......... 297/411.38 |
| 5,035,464 | A | * | 7/1991 | Spallholtz ................... 297/144 |
| 5,263,497 | A | | 11/1993 | Grabenkort et al. |
| 5,281,001 | A | * | 1/1994 | Bergsten et al. ....... 297/411.24 |
| 5,407,249 | A | * | 4/1995 | Bonutti .................. 297/411.35 |
| 5,462,247 | A | * | 10/1995 | Aldrich ....................... 248/118 |
| 5,489,143 | A | | 2/1996 | Adachi et al. |

(Continued)

*Primary Examiner*—Peter M. Cuomo
*Assistant Examiner*—Joe Edell
(74) *Attorney, Agent, or Firm*—Perkins Coie LLP

(57) ABSTRACT

An armrest assembly includes an armrest platform with hand and elbow extensions which is mounted to a swivel base unit that tilts, turns and rotates under the control of a single load control knob to permit placement of a patient's arm in several positions as needed to draw blood. The swivel base unit is mounted on the distal end of a cylindrical riser that can be raised and lowered to a desired elevation by a single load control lever supported by a base securing device that is adapted to be secured to different types of surfaces configurations.

2 Claims, 4 Drawing Sheets

U.S. PATENT DOCUMENTS

| | | | |
|---|---|---|---|
| D377,125 S * | 1/1997 | Adamsson | D6/418 |
| 5,623,951 A | 4/1997 | Kamaya | |
| 5,713,591 A * | 2/1998 | Zarkhin et al. | 280/250.1 |
| 5,803,642 A * | 9/1998 | Sassmannshausen | 403/90 |
| 5,845,643 A | 12/1998 | Vergano et al. | |
| 5,864,902 A | 2/1999 | Rogers | |
| 5,927,815 A * | 7/1999 | Nakamura et al. | 297/411.38 |
| 6,619,598 B1 * | 9/2003 | De Miranda | 248/118.3 |
| 6,619,747 B1 * | 9/2003 | Ko et al. | 297/423.12 |
| 6,663,055 B1 * | 12/2003 | Boucher et al. | 248/118 |

* cited by examiner

PHLEBOTOMY ARMREST ASSEMBLY AND METHOD OF USING SAME

FIELD OF THE INVENTION

The present invention relates to a device for facilitating phlebotomy procedures and more particularly to a phlebotomy armrest assembly that facilitates positioning and immobilizing a patient's arm in a fast and convenient manner.

BACKGROUND

Needlestick injuries occur with disconcerting frequency in healthcare facilities, and pose a major risk of transmission of AIDS and other viral diseases. These injuries most often occur in the setting of drawing blood specimens for laboratory testing. Skill and experience of the operator, and cooperation from the patient are factors that influence the occurrence of needlesticks. It is important to have adequate positioning of the patient's extremity while attempting phlebotomy. This allows a comfortable, unhurried approach by the phlebotomist, and decreases the likelihood of needlestick. Equally important is immobilization of the patient's extremity. Movement during the phlebotomy, especially sudden jerky movement is a prime cause of needlestick injury.

Therefore it would be highly desirable to have a new and improved phlebotomy armrest that permits placement of a patient's arm in several positions as needed to draw blood and that ensures that the patient will be comfortable without having to strain to maintain a desired position. Such a new and improved armrest should also be portable, and be able to be secured to different types of surface configurations.

SUMMARY OF THE INVENTION

An armrest platform assembly with hand and elbow extensions is mounted to a swivel base unit that turns and rotates under the control of a single load control knob to permit placement of a patients arm in several positions as needed to draw blood. The swivel base unit is mounted on the distal end of a cylindrical shaft that can be raised and lowered to a desired elevation by a single load control lever supported by a base securing device that is adapted to be secured to different types of surfaces configurations.

BRIEF DESCRIPTION OF THE DRAWINGS

The above mentioned features and steps of the invention and the manner of attaining them will become apparent, and the invention itself will be best understood by reference to the following description of the embodiments of the invention in conjunction with the accompanying drawings wherein.

DETAILED DESCRIPTION OF THE PREFERRED EMBODIMENTS

Figure 1:
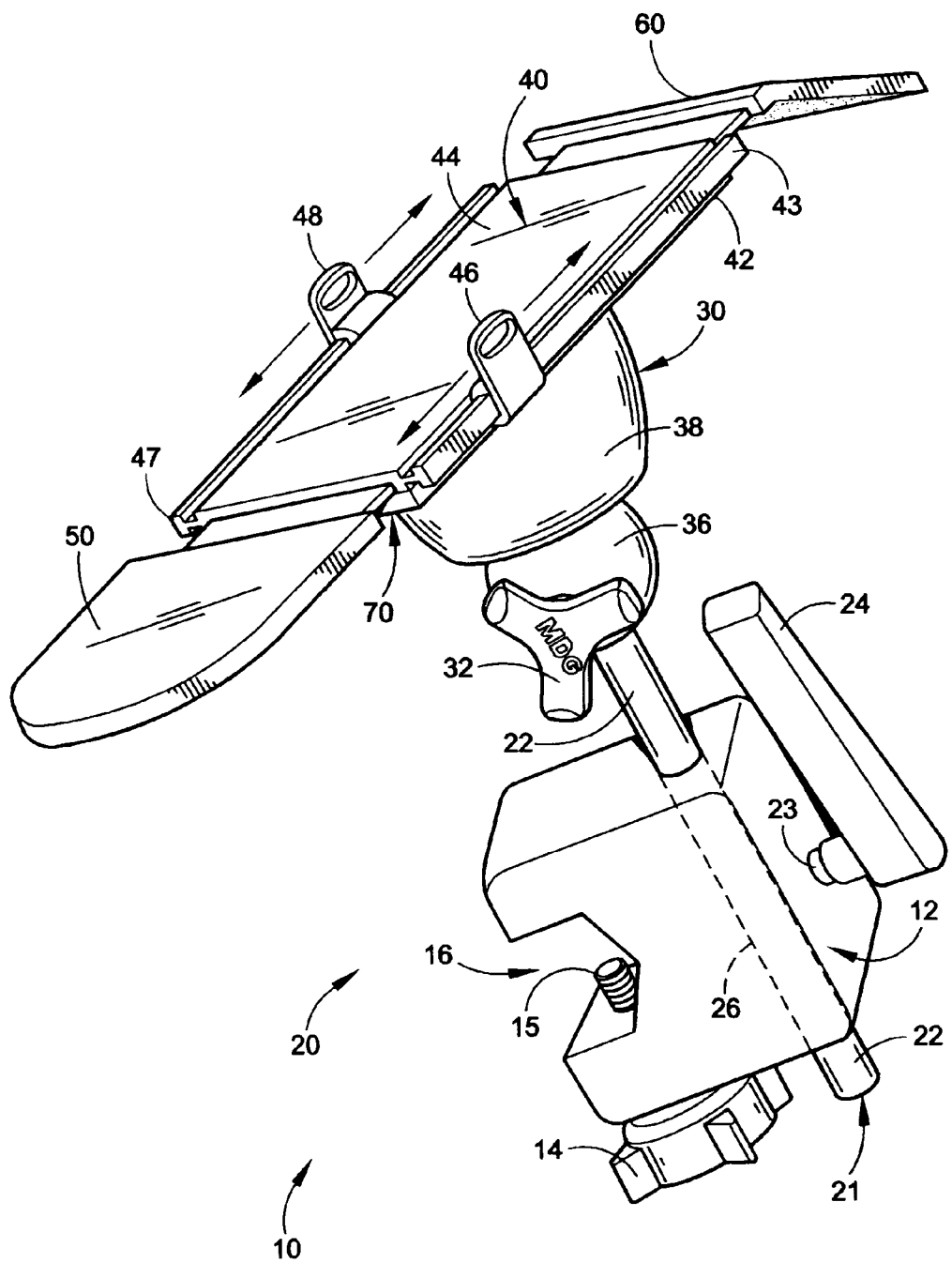
FIG. 1 is a perspective view of a phlebotomy armrest assembly, which is constructed in accordance with the present invention.

Referring now to the drawings and more particularly to FIGS. 1–4 thereof, there is illustrated a phlebotomy armrest assembly 10, which is constructed in accordance with the preferred embodiment of the present invention. As will be explained hereinafter in greater detail, the construction of the armrest assembly 10 is fashioned to accomplish two important functions: one to immobilize a patient's arm and two to permit placement of the patient's arm in any one of several positions as needed to draw blood, depending on the artery or vein, which is targeted by a clinician. Support from the armrest assembly 10 also ensures that the patient will be comfortable without having to strain to maintain a desired position.

Considering now the phlebotomy armrest assembly 10 in greater detail with reference to FIG. 1, the phlebotomy armrest assembly 10 includes an armrest platform assembly 40 that is supported from below by a universal adjustment arrangement 20 that is so constructed to help a clinical technician secure and place the arm of a patient in any one of a plurality of desired position planes relative to a supporting surface (not shown). In this regard, the universal adjustment arrangement 20 generally includes a lockdown base unit 12, and a swivel base unit 30, which supports from below the armrest platform assembly 40. The base unit 12 and the swivel base unit 30 cooperate together to help the clinical technician immobilize a patient's arm and then allows the technician to place the patient's arm in any one of several positions as needed to draw blood, depending on the artery or vein, which is targeted by a clinician.

Figure 2:
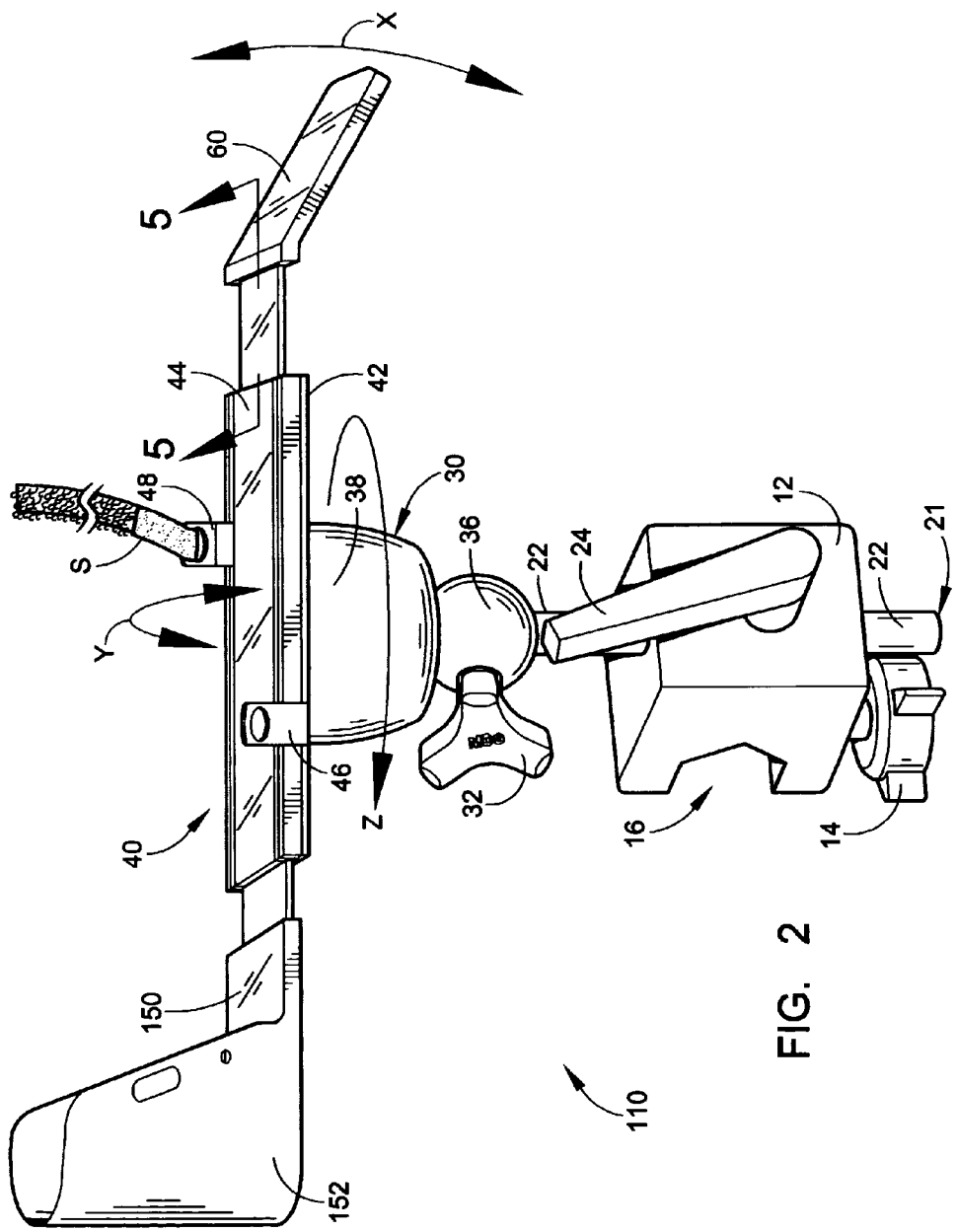
FIG. 2 is a perspective view of another phlebotomy armrest assembly, which is constructed in accordance with the present invention.

As best seen in FIGS. 1–2, the lockdown base unit 12 includes a clamping block 13 having a cutout 16, which is dimensioned for receiving a supporting surface extension. A large rotatable knob 14 having a centrally disposed screw 15 that extends into the cutout space 16 helps facilitate securing the lockdown base unit 12 in a fixed position to either a square frame supporting surface or a round frame supporting surface. Thus, for example, the phlebotomy armrest assembly 10 can be attached to a chair arm, a bedrail frame, a table, a wheelchair arm, or any other similar supporting surface having a square or round configuration.

In order to position a patient's arm at a desired height level relative to the supporting surface, the base unit 12 further includes an elevation control arrangement 20. The elevation control arrangement 21 has an elongated cylindrical riser 22 and a single load control lever 24 for helping the clinical technician set or position the armrest platform assembly 40 at a desired height relative to the supporting surface. The riser 22 is sufficiently long to extend between the lockdown base unit 12 and the swivel base unit 30. The riser 22 is slidably mounted within a riser passageway 26 disposed within the clamping block 13, and engages a stop 23, which is attached to a single load control lever 24. In this regard, the control lever 24 enables the stop 23 to frictionally engage and disengage the riser 22 so it can be raised or lower as it is moved along a rectilinear path of travel to a desired position relative to a supporting surface and then locked in position at a desired extension level relative to the supporting surface. The distal end of the riser 22 is received within a mounting hole 33 within the swivel base unit 30 and is secured within the hole 33 by a clamp 34.

Figure 3:
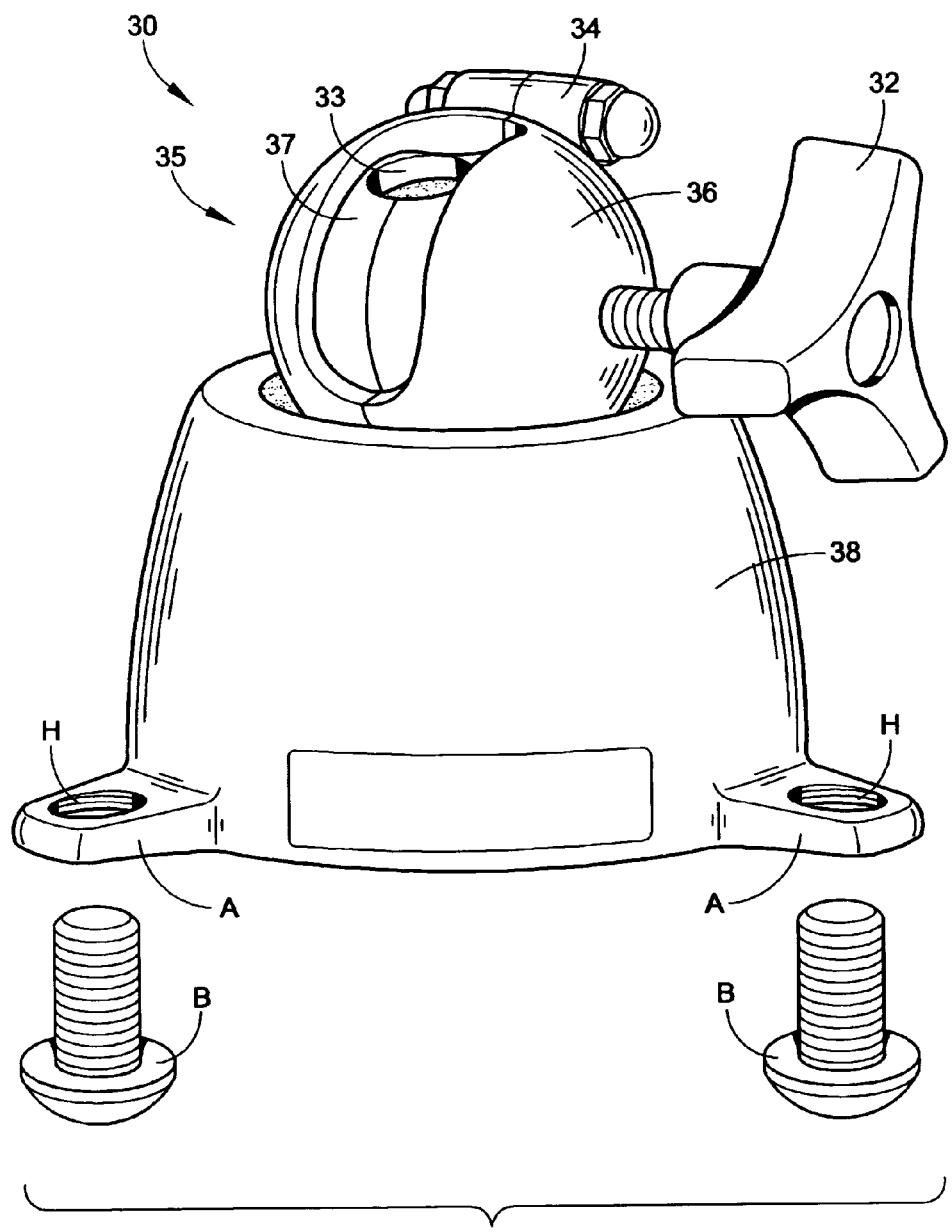
FIG. 3 is an enlarged view of a swivel base unit of FIG. 1.

Considering now the swivel base unit 30 in greater detail with reference to FIGS. 1 and 3, the swivel base unit 30 generally includes a housing 38 having mounted therein a split ball unit 35 having an outer ball 36 and an inner ball 37.

The outer ball 36 and the inner ball 37 are mounted for movement relative to one another so that the outer ball 36 tilts (180°), turns (180°) and rotates (180°) under the control of a single load control knob 32.

In this regard, the riser 22 mounted to the swivel base unit 30 can be rotated between about 0 degrees and about 180 degrees, turned between about 0 degrees and about 180 degrees, and tilted between about 0 degrees and about 180 degrees and then locked in a fixed desired position by locking the outer ball 36 and inner ball 37 together relative to the housing 38 using the knob 32.

The housing 38 includes a set of outwardly extending arms, such as arm A, where each arm A is countersunk with a bolt receiving hole H. In this regard, each hole H is dimensioned for receiving therein a bolt B that permit the housing 38 to be attached to the underside of the armrest platform assembly 40. It should suffice for the moment to mention that the phlebotomy armrest 10 provides a lightweight, comfortable platform for a patient's arm to rest within without strain, while simultaneously providing a clinician with a wide range of positioning options to facilitate attempting phlebotomy. This allows a comfortable, unhurried approach by the phlebotomist, and thus greatly decreases the likelihood of unwanted and undesired needlestick injuries. It should be noted that the swivel base unit 30, is a conventional part that is manufactured and sold by PanaVise located in Long Beach, Calif., with a url address of http:/www.panavise.com. The swivel base unit 30 is sold by PanaVise as its standard base Model 300. As the swivel base unit 30 is an off the self-item it will not be described hereinafter in greater detail.

Considering now the armrest platform assembly 40 in greater detail with reference to FIG. 1, the armrest slider assembly 40 generally includes a mounting platform 42 and an armrest platform 44. The armrest platform 44 has a hard, smooth non-textured surface that can be easily cleaned with any conventional disinfectant as required.

As best seen in FIG. 1, the mounting platform 42 and the armrest platform 44 are secured together to create an extension space indicated generally at 70 that is dimensioned for receiving at one of its open ends an elbow extension unit 50 and a hand extension unit 60 at another one of its open ends. In order to facilitate securing the swivel base unit housing 38 to the mounting platform 42, the mounting platform 42 includes a set of centrally disposed mounting holes (not shown). The mounting holes disposed within the mounting platform 42 are threaded and are dimensioned for receiving the bolts B. In this manner, the housing 38 can be fixed in a stationary position to the underside of the mounting platform 42.

As best seen in FIG. 1, the armrest platform 44 is generally rectangular in shape and includes a pair of spaced apart rail members 43 and 47 respectively. The rail members 43 and 47 are dimensioned for receiving thereon sliders 46 and 48 respectively. The sliders 46, 48 as best seen in FIG. 1, move in a rectilinear path along their rails members 42 and 43 so they can be positioned at any location along the longitudinal length of the armrest platform 44. Each of the sliders 46 and 48 includes a set screw (not shown) that allows a corresponding slider to be secured in a fixed position once it has been adjusted to a proper position for any given patient. Each slider, also has attached thereto, an immobilizing strap, such as the strap S as illustrated in FIG. 2, that can be used to immobilize the patients arm during the blood drawing procedure thereby helping to prevent unwanted and undesired sudden arm movement that could otherwise result in a needlestick injury.

Figure 5:
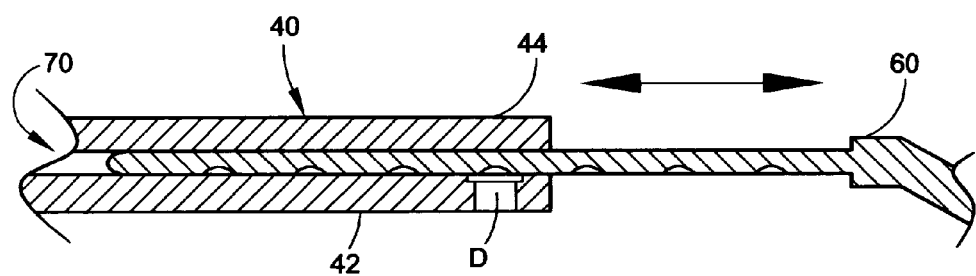
FIG. 5 is a cross sectional view of an armrest platform assembly taken along line 5—5 of FIG. 1.

The elbow extension 50 and hand extension 60 are captured within the interior of the extension space 70 between the mounting platform 42 and the armrest platform 44. In this regard, the extensions 50 and 60 slide out from the extension space 70 in incremental steps. That is, as an extension, such as the extension 50 as best seen in FIG. 5, is pulled from the interior of the extension space 70a detent D, which can be depressed by a user causes the extension 50 to step from one locking position to another locking position until the extension 50 is extended to its fully extended position, which is also a locked position that prevents the extension 50 from being further extended from the extension space. The extension 60 is pulled under the hand force of a technician in a similar manner as described for extension 50.

Considering now the method of using the armrest assembly 10 in greater detail, the technician first secures the lockdown base unit 12 to a stationary surface, such as a chair, bed or table, by engaging the stationary surface with the screw 15 with a sufficient force using the control knob 14 to lock the base unit 12 in place relative to the stationary surface.

Next the technician releases the control lever 24 so that the riser 22 is free to slide within the lockdown base unit 12. With the riser 22 free to slide within the lockdown base unit 12, the technician adjusts the space between the lockdown base unit 13 and the armrest assembly 40 so that the armrest platform 44 is properly positioned to receive thereon the forearm of a patient. When the armrest platform 44 is properly positioned, the technician pushes the control lever 24 into its locked positions as best seen in FIG. 1 causing the riser 22 to be locked into position.

Next, the technician has the patient place his or her forearm onto the armrest platform 44 and then adjusts the elbow extension 50 and the hand extension 60 for the comfort of the patient. Next, the technician moves the sliders 46 and 48 to a desired position relative to the forearm of the patient and then secured them on their respective rails 43 and 47 by use of the setscrews. The technician then, using the immobilization straps S secures the patient's forearm to the armrest platform 44.

Finally, the technician releases the load control knob 32 and adjust the arm rest platform 44 to a final position for extracting blood from the patent by tilting, turning and rotating the platform 44 to its desired final position. When so positioned, the technician closes the load control knob 32 so the armrest platform is locked into position.

Figure 4:
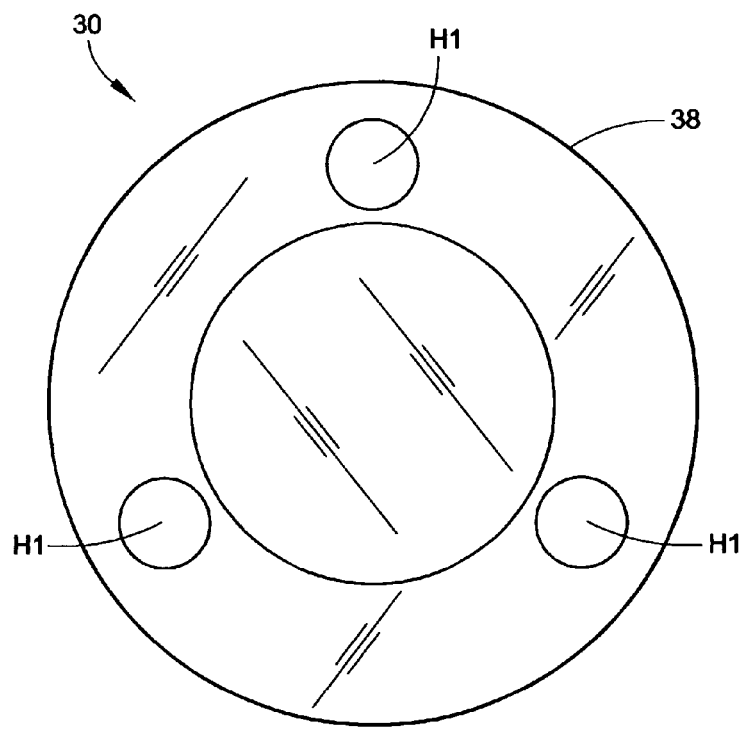
FIG. 4 is an enlarged bottom plane view of a swivel base unit housing of FIG. 2.

Referring now to the drawings and more particularly to FIGS. 2 and 4, there is illustrated another phlebotomy armrest assembly 110, which is constructed in accordance with the present invention. The armrest assembly is identical in construction to the armrest assembly 10 with the exception of the swivel base unit 130. In this regard, the feature reference characters used to describe the armrest assembly 10 are used to describe the armrest assembly 100 except for where there is a difference.

Considering the armrest assembly 110 in greater detail with reference to FIGS. 2 and 4, the armrest assembly 110 includes an adjustable cylindrical riser 22 that is fixed at one of its end in a swivel base unit 130 and slidably mounted at the other one of its ends in a lockdown base unit 12. The swivel base unit 130 is identical in construction to the swivel base unit 30 except for its housing. In the regard, the swivel base unit 130 includes a housing 138 having a set of mounting holes, such as the mounting holes H1, which are disposed in the base of the housing 138. This arrangement provides a smaller foot print for the swivel base unit 130, as opposed to the swivel base unit 30, thereby allowing the width dimension of the mounting platform 142 and the armrest platform 144 to be substantially less than that of the mounting platform 42 and the armrest platform 44 of the armrest assembly 10.

Considering the armrest assembly 110 in still greater detail, as best seen in FIG. 2, the assembly 110 further includes an elbow extension 150 that includes a raised guard or wall 152 to prevent the arm of the patient from sliding off the assembly 110 when the armrest platform is raised upward from the horizontal. This adds an extra degree of safety to using the assembly 110.

Although in the preferred embodiment of the present invention the armrest platform 44 is described as a flat unprotected arm receiving surface, it is contemplated within the scope of the present invention, that the armrest platform 44 could also be a padded surface to add extra comfort for a patient. Thus, while particular embodiments of the present invention have been disclosed, it is to be understood that various different modifications are possible and are contemplated within the true spirit and scope of the appended claims. There is no intention, therefore, of limitations to the exact abstract or disclosure herein presented.

I claim:

1. A phlebotomy armrest to help facilitate drawing blood from the arm of a patient, comprising:

an armrest supported from below by a universal adjustment arrangement to place the arm of the patient in any one of a plurality of desired position planes relative to a supporting surface;

said universal adjustment arrangement including a housing removably mounted to said armrest;

said housing having disposed therein an outer ball and an inner ball mounted for universal movement relative to one another;

a riser, wherein said inner ball has a first securing arrangement for securing the riser to said inner ball, wherein said first securing arrangement is mounted on a distal end portion of the riser and releasably secures the inner ball by clamping the outer ball around the inner ball; and said outer ball having a second securing arrangement for securing said outer ball in a fixed position relative to said inner ball, and wherein said outer ball includes a control knob for securing said armrest in said any one of a plurality of desired position planes relative to the supporting surface.

2. The phlebotomy armrest according to claim 1, wherein said riser is secured to a single load control lever that facilitates raising and lowering said riser and locking said riser in position so that said armrest is placed in said any one of a plurality of desired position planes relative to the supporting surface.

* * * * *

UNITED STATES PATENT AND TRADEMARK OFFICE
CERTIFICATE OF CORRECTION

PATENT NO. : 7,055,910 B2
APPLICATION NO. : 10/655148
DATED : June 6, 2006
INVENTOR(S) : Clifford A. Wright It is certified that error appears in the above-identified patent and that said Letters Patent is hereby corrected as shown below:

Column 6, line 12, the text reading "clamping the outer ball around the inner ball" should be followed by --, and wherein the riser travels along a rectilinear path to raise and lower the armrest to facilitate placing the arm of the patient in said plurality of desired position planes relative to the supporting surface--

Signed and Sealed this

Ninth Day of January, 2007

JON W. DUDAS
*Director of the United States Patent and Trademark Office*